United States Patent [19]
Marchand et al.

[11] Patent Number: 4,564,005
[45] Date of Patent: Jan. 14, 1986

[54] ORAL IRRIGATING DEVICE

[76] Inventors: Paul A. Marchand, 1171 71st St., Miami Beach, Fla. 33141; Noel W. Abramson, 830 W. 32 St., Hialeah, Fla. 33012

[21] Appl. No.: 558,039

[22] Filed: Dec. 5, 1983

[51] Int. Cl.⁴ ............................................. A61M 3/00
[52] U.S. Cl. ..................................... 128/66; 604/84; D604/150
[58] Field of Search .............. 128/66, 62 A, 229, 230, 128/231

[56] References Cited
U.S. PATENT DOCUMENTS 4,043,337  8/1977  Baugher ................................ 128/66
4,458,676  7/1984  Pileggi ................................... 128/66

Primary Examiner—Robert Peshock
Attorney, Agent, or Firm—John Cyril Malloy

[57] ABSTRACT

An oral irrigation assembly of the type designed to be used in combination with a conventional water outlet such as an outlet associated with a showerhead or like water dispersement means. A water conduit includes a first and second channel structured to deliver water concurrently to the showerhead and to an assembly specifically structured to cause pulsing water flow to issue from the water conduit to an irrigating applicator preferably in the form of a nozzle or the like. A valve structure is disposed in water regulating relation to the second channel such that water flow may be selectively stopped when use of the oral irrigating device is not desired but water flow from the showerhead is maintained.

11 Claims, 5 Drawing Figures

ORAL IRRIGATING DEVICE

BACKGROUND OF THE INVENTION

1. Field of the Invention

This invention is directed towards an oral irrigating device designed to clean the teeth and stimulate the gums wherein the assembly is used in combination with a conventional water outlet such as a showerhead. Both the irrigating assembly and the showerhead may be operated simultaneously or alternately and the irrigating assembly may be selectively rendered inactive when one desires just to take a shower.

2. Description of the Prior Art

For many years it has been acknowledged that healthy gums and teeth can only be accomplished through the performance and maintenance of proper dental hygiene. Typically, such hygienic steps include the use of a hand or mechanically manipulated toothbrush wherein toothpaste or gels including various ingredients are applied to the brush head and thereby applied directly to the teeth and the junction of the gums and the teeth. Recent studies by the dentistry profession have recognized the limitations in the brushing method and, as a result, have begun professing the use of oral hydraulic irrigators. While such irrigators have been in use for many years in the dentist's office during dental treatment and for cleaning and massaging gums, such oral irrigation devices have only recently been available to the general public.

Accordingly, consumer products are currently available on the market which have adopted this dental irrigation technique for every day use in cleaning teeth. The majority of such devices which are available to the consumer utilizes a pulsating pressure for propelling water against the teeth and against the gums and crevices primarily for the purpose of massage and for dislodging debris and food particles.

Certain disadvantages have become apparent however with the use of such commercially available products. Typically, a supply of water is secured to a pumping device which directs water or fluid flow in a pulsating fashion to designated portions of the teeth, mouth and supporting gum structure. Other problems associated with prior art devices include spilling and splattering of pulsating droplets from the teeth. Such splattering as well as the accumulation of liquid within the mouth frequently causes unsightly spillage even when the irrigator or nozzle portion thereof is used over a sink area or like receptacle. Frequently such spillage, splatter and the like results in an unwanted and an unsightly dispersement of fluid about the general sink and/or receptacle area.

Prior art devices of the type described above are evidenced in the U.S. patents to Heitzman, U.S. Pat. No. 3,468,306; Baugher, U.S. Pat. No. 4,043,337; and Rice, U.S. Pat. No. 4,265,229.

In order to overcome these problems, prior art devices have been developed wherein oral irrigating assemblies are used in combination with or attached to water outlets generally associated with showerheads to the extent that the process of oral irrigation takes place within the tub during, before or after activating of the shower.

SUMMARY OF THE INVENTION

This invention is directed toward an oral irrigation assembly of the type used to clean food particles and plaque from the teeth and gums by the direction of a pulsating flow of liquid or water to the interior of the mouth. The device further has the ability to provide a certain amount of massage for gum stimulation. More specifically, the subject oral irrigation assembly is primarily designed for use in combination with a conventional water outlet of the type generally associated with showerheads or like water dispersement means. By virtue of this application, the process of oral irrigation takes place within a bathtub or like large receptacle thereby preventing unsightly and undesirable splashing, splattering and spillage frequently associated with numerous prior art devices.

To accomplish the above, the subject oral irrigation assembly comprises a water conduit means affixed preferably at one end to a conventional water supply such as the type associated with domestic water supplies for houses and like dwellings. In the preferred embodiment of the present invention, the water conduit means is connected to or serves to support a water dispersement means of substantially conventional design and structure such as a showerhead or the like. Further, the water conduit means includes a substantially hollow interior portion defining a first channel extending in direct water communication between the conventional water supply and the showerhead or like dispersement structure.

The water conduit means includes a second channel itself being divided into a first channel segment and a second channel segment, both of which by virtue of their substantially common displacement within the second channel means, being connected in liquid receiving relation to the conventional water supply. In addition, both are structured to define segregated paths of water flow from the conventional water supply to a water pulsing means.

The water pulsing means preferably comprises a turbine disk or structure having a periphery structured to include inserts and/or fins wherein the periphery is disposed in interruptive engagement or contact with water flow passing along and through the first channel segment. Peripheral engagement with this water flow causes the continuous rotation of the turbine structure as long as water flow through the first channel segment is maintained.

The second channel segment serves to direct a path of water flow into engagement with a base portion of the turbine structure and more specifically into fluid communication with a plurality of passage structures formed in and structured to pass through the base portion of the turbine structure. A plurality of the passage structures are disposed in spaced apart relation to one another and are extended through the base portion in a substantially transverse orientation relative to the plane of rotation of the turbine structure upon its periphery engaging the path of water flow through the first channel segment as set forth above. Accordingly, the individual passage structures pass into direct fluid receiving and communicating relation with water issuing from the first channel segment in successive fashion. This successive passage to and from direct liquid communication serves to produce a pulsating flow issuing from the turbine structure.

A delivery conduit and/or tubing extends from a location exteriorly of the water conduit means but in path defining relation to the pulsating flow of water issuing from the turbine structure. An applicator nozzle or like applicator means is structured to receive the pulsating flow from the delivery conduit or tubing and serves to direct the pulsating flow to the individual selected locations on the interior of the mouth.

Other structural features of the present invention include the provision of a compartment formed of porous material maintained on the interior of the applicator nozzle wherein dentifrice or like cleansing material or tablets are disposed within the compartment and serve to mix with the water passing through the body of the applicator nozzle for more efficient and effective cleaning and/or oral irrigation of the mouth interior during operation of the subject assembly.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference is had to the following detailed description taken in connection with the accompanying drawings, in which.

Like reference numerals refer to like parts throughout the several views of the drawings.

DETAILED DESCRIPTION OF THE PREFERRED EMBODIMENT

Figure 1:
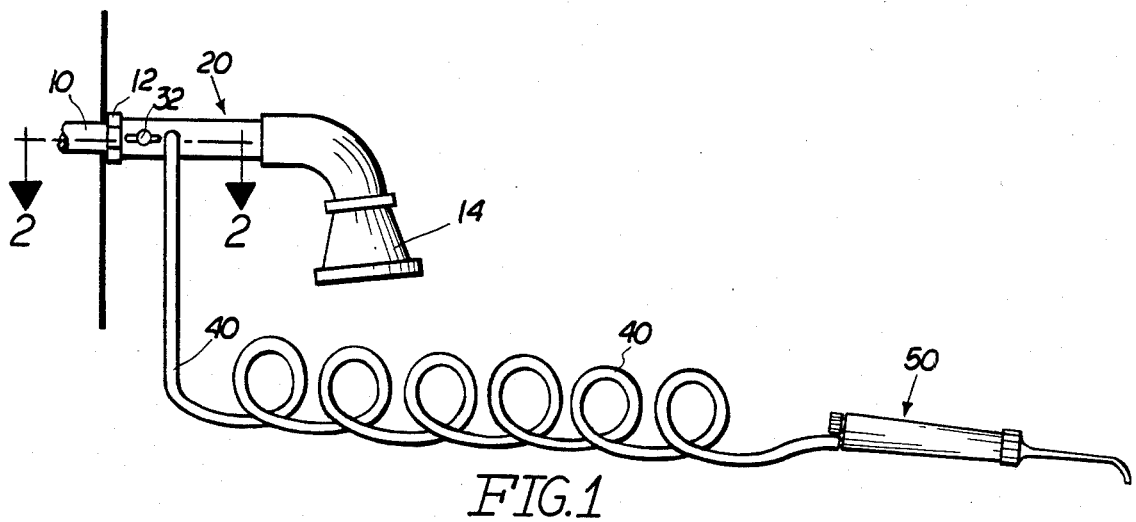
FIG. 1 is a side plan view in partial cutaway showing attachment of the irrigating assembly to a conventional water outlet including a showerhead or like dispensing structure.

With reference to FIG. 1, the present invention is directed towards an oral irrigating assembly incorporating an applicator nozzle 50 interconnected to a conduit means generally indicated as 20 by a delivery conduit 40. A conventional water supply 10 such as from municipal hook-ups to a local resident or commercial dwelling is interconnected in water communication with the conduit means 20 by means of a connector element 12 which also may be well known in the art.

Figure 2:
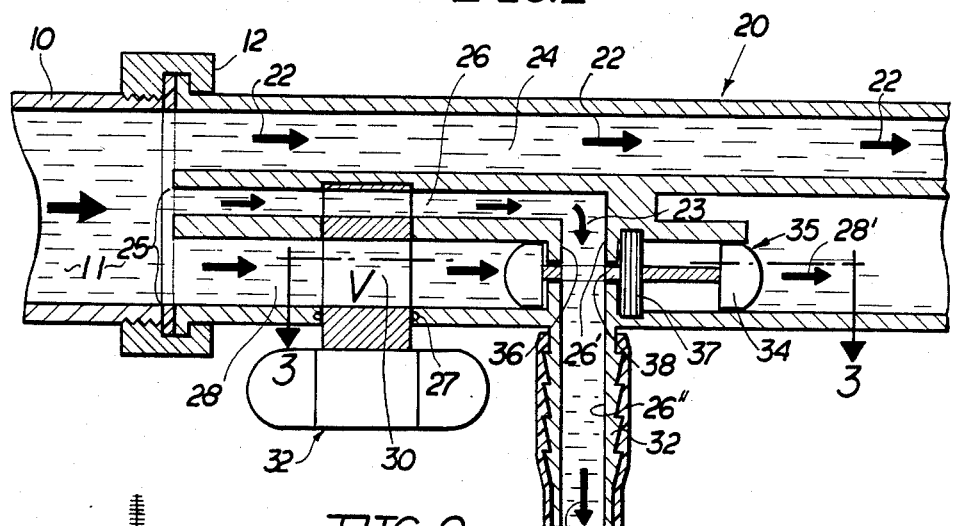
FIG. 2 is a sectional view of the water conduit showing individual water paths of travel as they issue from a conventional water supply.

With reference to FIG. 2, water 11 from a conventional supply represented by conduit 10 passes into the water conduit means 20. This water conduit means includes a hollow interior portion including a first channel means 24 structured to direct a path of water flow indicated by directional arrows 22 therethrough to a delivery portion of the conduit which is attached to a substantially conventional water dispensing means such as showerhead 14 (see FIG. 1). Control of water flow through the conduit means 20 from the water supply 10 is regulated in the conventional fashion through on/off nozzles normally associated with showers of conventional design.

The conduit means 20 further includes a second channel means 25 including a first channel segment 26 and a second channel segment 28. Water through both of these channel segments may be controlled through an on/off valve structure extending physically across the flow path and interior of both the first and second channel segments 26 and 28. An on/off activator knob 32 extends outwardly from the liquid conduit means 20 as from the side thereof so as to allow shut-off of water through the second channel means 25 while maintaining water flow through the first channel means 24. This enables the water to be dispensed from the showerhead 14 in the normal fashion when it is not desired to operate or activate the oral irrigating assembly.

Figure 3:
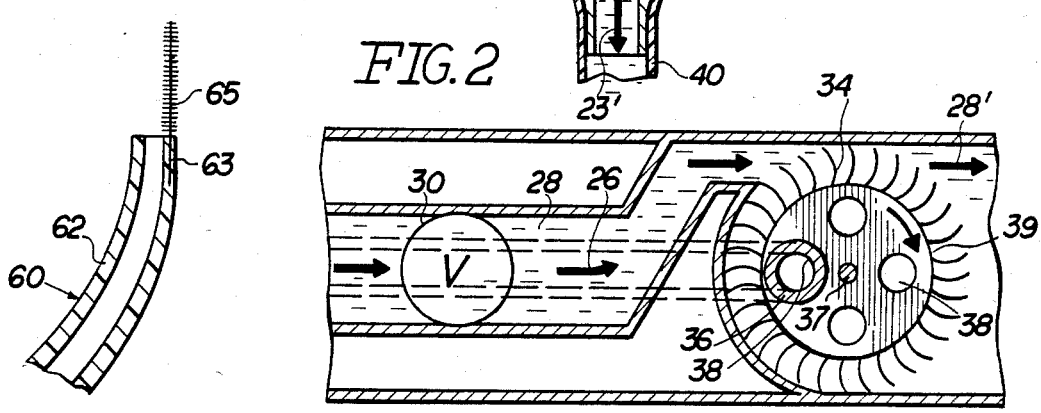
FIG. 3 is a detailed view in section showing structural details and/or relative locations of the turbine structure to cause pulsed flow.

However, when activation of the irrigating assembly is desired, the knob 32 is placed in its on or activating position so as to allow water flow through the valve structure 30 and more specifically through each of the first and second channel segments 26 and 28. Second channel segment 28 (FIG. 3) is structured to direct fluid flow about the periphery of a water pulsing means generally indicated as 35. The water pulsing means may be in the form of a turbine type element rotatably mounted as at 38 on the interior of the second channel means and in specific interruptive engagement with both the first and second channel segments 26 and 28. As set forth above and as clearly outlined in FIG. 3, when valve 30 is in its open position water flow will pass, as indicated by directional arrows 31 in interruptive, and in driving engagement with the periphery of the pulsing means 35. Sealing means is provided in the form of an O-ring 27 mounted in an appropriately positioned nesting groove to prevent leakage of water from conduit means 20. The periphery may include veins or wing-tipped structures 34 which are specifically configured to be driven by the interruptive engagement of the water flow about the periphery of the pulsing means 35. This of course causes rotation of the element about pin or like mounting member 37. After driving engagement of the periphery of the water pulsing means 35, the water flow is directed as at 28' beyond the water pulsing means 35 and to the delivery portion of the conduit 20 (see FIG. 3).

An important feature of the present invention is the provision of passage means integrally formed in the base 39 of the pulsing means 35. The passage means includes a plurality of passage structures 38 extending through the entire base and more specifically disposed in substantially equally spaced apart relation. Each of the passage structures 38 are designed to successively pass into and accordingly become a part of the water flow 23 passing along the first channel segment 26 when the valve structure 30 is in its open position. It is to be noted that in the embodiment shown in FIG. 2, the path of water flow defined by the first channel segment 26 is directed, at least in part, substantially transverse to the plane of rotation of the base 39 of the pulsing means 35. Accordingly, the passage structures 38 will successively come into registry with the transverse portion 26' of the first channel segment 26 thereby allowing water to pass therethrough and continue to pass along the remaining portion 26" of the second channel segment. However, since the flow of water is periodically and successively interrupted, water flow indicated by directional arrow 23' will be in a pulsed or pulsing state. This pulsing state will continue throughout the length of the delivery conduit 40 and into the applicator nozzle 50. Water will then issue from nozzle tip generally indicated as 60 and the nozzle tip 62. Attachment of the nozzle 60 to the nozzle body 50 may be by conventional threaded fastener as at 64. Further, a porous or cage-like container 58 is mounted on the interior of the body 52 of the applicator nozzle 50. An opening element 54 in the form of a screw threaded plug or like may be removed so as to fit in dentifrice, cleansing material or like tablets 60. Due to the open mesh construction of the cage or compartment 58, the water entering portion 56 from delivery conduit 40 will mix with the added material 60 and will blend with the water briefly maintained on the interior of the body 52. Accordingly, when the water exits from the nozzle tip 62 to any portion of the mouth, dentrifice, cleanser or like additive may also be directed to these internal portions.

Figure 5:
FIG. 5 is a partial view similar to the right side of FIG. 4 illustrating a brush on the distal end of the nozzle.
Figure 4:
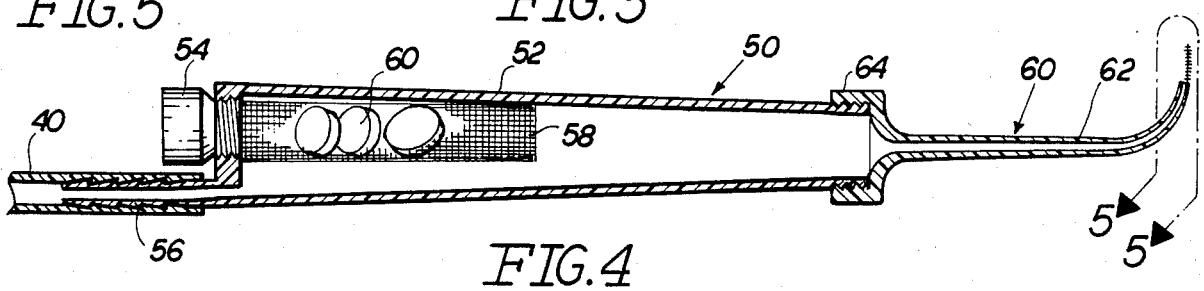
FIG. 4 is a detailed view in section showing structural components and further detail of the applicator nozzle of the present invention.

With respect to FIG. 5, the brush 65 has a stem which is secured to the nozzle for example by embedding the stem 63 in the plastic wall of the nozzle. It is a connection brush used to clean interproximal area between teeth and under fixed bridgework, a condition typical of older patients. Various types of suitable tips may be used to meet the patient's individual periodontal condition, for example, an elongated distal end with a fine diameter mouth may be used to reach relatively deep periodontal patients.

It will be seen that the basis of the present invention made apparent from the preceding description is efficiently attained and since certain changes may be made in the above contruction without departing from the scope of the inventtion, it is intended that all matter contained in the above description or shown in the accompanying drawings shall be interpreted as illustrative and not in a limiting sense.

Now that the invention has been described, what is claimed is:

1. An oral irrigating assembly of the type primarily designed for use with a substantially conventional water outlet, the assembly comprising:
    (a) conduit means secured to a conventional water supply and structured for delivery of water therefrom,
    (b) said water conduit means comprising a hollow interior portion including a first channel means extending along at least a portion of the length thereof and disposed for water delivery from the water supply to a delivery portion of said conduit means,
    (c) a second channel means formed within said hollow interior portion and structured and disposed for water delivery from the water supply to an exterior of said conduit means, said second channel means structured to define diverse paths of liquid flow therethrough,
    (d) water pulsing means movably mounted within said hollow interior portion in interruptive relation to said diverse paths of liquid flow,
    (e) said diverse paths of liquid flow comprising a first channel segment and a second channel segment at least partially disposed in spaced relation to one another and each structured to define a path of liquid flow from the water supply to said water pulsing means,
    (f) said second channel segment disposed to direct liquid flow into driving engagement with said water pulsing means, causing its rotation, said first channel segment disposed to direct water flow into flow regulating engagement with said water pulsing means,
    (g) said water pulsing means disposed in interruptive relation to liquid flow from said first channel segment and structured to alternately stop and pass said liquid flow beyond said water pulsing means,
    (h) said first and said second channel segments and said water pulsing means cooperatively disposed and struc tured to cause a pulsed liquid flow from said first channel segment concurrently to driving rotation of said water pulsing means by liquid flow from said second channel segment.

2. An assembly as in claim 1 further comprising nozzle means interconnected in liquid communication to said water pulsing means and said second channel means.

3. An assembly as in claim 1 further comprising flow control means disposed in flow regulating position between a water supply and at least a portion of said second channel means, and structured to selectively stop water flow through at least a portion of said second channel means.

4. An assembly as in claim 3 wherein said flow control means comprises a valve structure at least partially disposed in water flow regulating relation between the water supply and said diverse paths of liquid flow and to said water pulsing means.

5. An assembly as in claim 1 wherein said second channel segment is disposed to direct liquid flow substantially tangentially of said water pulsing means and in interruptive, driving engagement with the periphery thereof.

6. An assembly as in claim 5 wherein said water pulsing means is rotatably mounted within said second channel means and comprises an outer periphery, structured and disposed for interruptive and rotatably driven contact by water flow through said second channel segment.

7. An assembly as in claim 6 wherein said pulsing means comprises a base portion structured to include said outer periphery formed thereabout; passage means formed in said base portion in substantially transverse relation to a plane of rotation of said base portion and in liquid communicating relation with said first channel segment.

8. An assembly as in claim 7 wherein said first channel segment defines a path of liquid flow from the water supply to said base portion and said passage means formed therein.

9. An assembly as in claim 8 wherein said passage means comprises a plurality of passage structures each spaced from one another and each extending through said base portion in transverse relation to a plane of rotation thereof, each of said passage structures successively positioned into fluid communicating relation with said first channel segment so as to successively direct liquid flow from said first channel segment through said water pulsing means.

10. An assembly as in claim 9 wherein said passage structures are integrally formed in said base portion to pass therethrough, said second channel segment and said passage means cooperatively disposed to define pulsing liquid flow through said base portion and direct said pulsing liquid flow exteriorly of said conduit means.

11. An assembly as in claim 6 wherein said first channel segment and said second channel segment are disposed in substantially common liquid communication with the water supply and structured to define separate and concurrent paths of water flow therefrom to said outer periphery and said passage means of said base portion respectively, whereby pulsing flow of water selectively issues from said water conduit means.

* * * * *